United States Patent [19]

Seward et al.

[11] Patent Number: 5,699,805
[45] Date of Patent: Dec. 23, 1997

[54] LONGITUDINAL MULTIPLANE ULTRASOUND TRANSDUCER UNDERFLUID CATHETER SYSTEM

[75] Inventors: James Bernard Seward; Abdul Jamil Tajik, both of Rochester, Minn.

[73] Assignee: Mayo Foundation for Medical Education and Research, Rochester, Minn.

[21] Appl. No.: 668,103

[22] Filed: Jun. 20, 1996

[51] Int. Cl.$^6$ ..................................................... A61B 8/12
[52] U.S. Cl. .................. 128/662.06; 128/662.03; 128/661.01
[58] Field of Search .................. 128/662.06, 662.03, 128/661.01, 660.08, 916

[56] References Cited

U.S. PATENT DOCUMENTS

| | | | |
|---|---|---|---|
| 3,789,833 | 2/1974 | Bom . | |
| 3,938,502 | 2/1976 | Bom . | |
| 4,028,934 | 6/1977 | Sollish . | |
| 4,462,408 | 7/1984 | Silverstein et al. . | |
| 4,543,960 | 10/1985 | Harui et al. | 128/660 |
| 4,550,607 | 11/1985 | Maslak et al. | 73/626 |
| 4,582,067 | 4/1986 | Silverstein et al. | 128/663 |
| 4,699,009 | 10/1987 | Maslak et al. | 73/626 |
| 4,771,788 | 9/1988 | Millar | 128/661.09 |
| 4,794,931 | 1/1989 | Yock | 128/660.03 |
| 4,802,487 | 2/1989 | Martin et al. . | |
| 4,841,977 | 6/1989 | Griffith et al. | 128/344 |
| 4,887,605 | 12/1989 | Angelsen et al. | 128/660.03 |
| 4,911,170 | 3/1990 | Thomas, III et al. | 128/662.06 |
| 4,917,097 | 4/1990 | Proudian et al. | 128/662.06 |

(List continued on next page.)

FOREIGN PATENT DOCUMENTS

| | | |
|---|---|---|
| 0 600 568 | 6/1994 | European Pat. Off. . |
| WO 90/13260 | 11/1990 | WIPO . |
| WO 91/04707 | 4/1991 | WIPO . |
| WO 95/19143 | 7/1995 | WIPO . |
| WO 96/00522 | 1/1996 | WIPO . |
| WO 96/03918 | 2/1996 | WIPO . |
| WO 96/03921 | 2/1996 | WIPO . |
| WO 96/03922 | 2/1996 | WIPO . |
| WO 96/04588 | 2/1996 | WIPO . |

OTHER PUBLICATIONS

Weintraub et al., "Realtimes Intracardiac Two–Dimensional Echocardiography in the Catheterization Laboratory in Humans". Abstract *JACC* vol. 15, No. 2, 16A (Feb. 1990).

Pandian et al., "Intracardiac Echocardiography. Experimental Observations on Intracavitary Imaging of Cardiac Structures with 20–MHz Ultrasound Catheters", *Echocardiography*, vol. 8, No. 1 (Jan. 1991) pp. 127–134.

Seward et al., "Transvascular and Intracardiac Two–Dimensional Echocardiorgraphy", *Echocardiography*, vol. 7, No. 4 (Jul. 1990) pp. 457–464.

(List continued on next page.)

*Primary Examiner*—Marvin M. Lateef
*Assistant Examiner*—Derrick Fields
*Attorney, Agent, or Firm*—Merchant, Gould, Smith, Edell, Welter & Schmidt, P.A.

[57] ABSTRACT

An underfluid imaging, diagnostic, interventional, or measuring catheter apparatus including an outer catheter body and a drive shaft receivable in the outer body and rotatable with respect to the outer body; an ultrasound transducer array mounted on the rotatable drive shaft and rotated with the drive shaft; and a ultrasound window portion disposed on the outer body, wherein the ultrasound transducer array is longitudinally positionable within the outer body proximate the window portion so as to allow transmission of ultrasound signals from the transducer array to the outside of the catheter. The ultrasound signals are a sequential set of spatially related tomographic image planes which define a volumetric field of view around the catheter. An underfluid therapeutic or diagnostic device can be received in the catheter through a port extending from proximate a proximal end to proximate a distal end of the catheter. The device is operated in the volumetric field of view which provides a real time image of the operation.

19 Claims, 4 Drawing Sheets

U.S. PATENT DOCUMENTS

| | | | |
|---|---|---|---|
| 4,936,281 | 6/1990 | Stasz | 128/660.03 |
| 4,947,852 | 8/1990 | Nassi et al. | 128/662.06 |
| 4,951,677 | 8/1990 | Crowley et al. | 128/662.06 |
| 4,957,111 | 9/1990 | Millar | 128/662.06 |
| 5,002,059 | 3/1991 | Crowley et al. | 128/662.06 |
| 5,014,710 | 5/1991 | Maslak et al. | 128/660.05 |
| 5,022,399 | 6/1991 | Biegeleisen | 128/662.06 |
| 5,029,588 | 7/1991 | Yock et al. | 128/662.06 |
| 5,038,789 | 8/1991 | Frazin | 128/662.06 |
| 5,070,879 | 12/1991 | Herres | |
| 5,076,278 | 12/1991 | Vilkomerson et al. | 128/662.03 |
| 5,076,279 | 12/1991 | Arenson et al. | 128/662.05 |
| 5,081,993 | 1/1992 | Kitney et al. | |
| 5,105,819 | 4/1992 | Wollschläger et al. | 128/662.06 |
| 5,125,410 | 6/1992 | Misono et al. | 128/662.06 |
| 5,140,558 | 8/1992 | Harrison, Jr. et al. | 367/7 |
| 5,148,810 | 9/1992 | Maslak et al. | 128/661.01 |
| 5,161,537 | 11/1992 | Hashimoto et al. | 128/662.06 |
| 5,165,413 | 11/1992 | Maslak et al. | 128/660.05 |
| 5,186,175 | 2/1993 | Hirama et al. | |
| 5,186,177 | 2/1993 | O'Donnell et al. | 128/662.06 |
| 5,193,546 | 3/1993 | Shaknovich | 128/662.06 |
| 5,199,437 | 4/1993 | Langberg | 128/662.06 |
| 5,211,168 | 5/1993 | Mason et al. | |
| 5,222,501 | 6/1993 | Ideker et al. | 128/660.03 |
| 5,235,986 | 8/1993 | Maslak et al. | 128/661.01 |
| 5,261,408 | 11/1993 | Maslak et al. | 128/661.01 |
| 5,285,788 | 2/1994 | Arenson et al. | 128/660.05 |
| 5,291,893 | 3/1994 | Slayton | 128/662.06 |
| 5,297,553 | 3/1994 | Sliwa, Jr. et al. | 128/662.03 |
| 5,305,756 | 4/1994 | Entrekin et al. | 128/660.09 |
| 5,311,871 | 5/1994 | Yock | 128/662.95 |
| 5,325,860 | 7/1994 | Seward et al. | 128/662.06 |
| 5,329,496 | 7/1994 | Smith | 367/140 |
| 5,345,940 | 9/1994 | Seward et al. | 128/662.06 |
| 5,360,007 | 11/1994 | Shinomura et al. | 128/662.06 |
| 5,373,845 | 12/1994 | Gardineer et al. | 128/660.09 |
| 5,385,148 | 1/1995 | Lesh et al. | 128/662.06 |
| 5,415,175 | 5/1995 | Hanafy et al. | 128/662.03 |
| 5,438,998 | 8/1995 | Hanafy | 128/662.03 |
| 5,460,181 | 10/1995 | Seyed-Bolorforosh | |
| 5,465,724 | 11/1995 | Sliwa, Jr. et al. | 128/662.03 |
| 5,503,152 | 4/1996 | Oakley et al. | |
| 5,549,111 | 8/1996 | Wright et al. | 128/742 |

OTHER PUBLICATIONS

Schwartz et al., "Real–Time Intracardiac Two–Dimensional Echocardiography: An Experimental Study of In Vivo Feasibility, Imaging Planes, and Echocardiographic Anatomy", *Echocardiography*, vol. 7, No. 4 (1990) pp. 443–455.

Schwartz et al., "Intracardiac Echocardiography in Humans Using a Small Sized (6F), Low Frequency (12.5 MHz) Ultrasound Catheter", *JACC*, vol. 21, No. 1–(Jan. 1993) pp. 189–198.

"Cardiovascular Imaging Systems' Intracardiac Imaging Catheter", *M–D–D–I Reports*, publisher: F–D–C Reports, Inc., pp. I&W–6 and I&W–7 (Mar. 30, 1992).

Moriuchi et al., "Transvenous Echocardiography: Experimental Feasibility Study", *Jpn J Med Ultrasonics*, vol. 19, No. 3 (1992), pp. 228–235.

Nishimura et al., "Intravascular Ultrasound Imaging: In Vitro Validation and Pathologic Correlation", *JACC*, vol. 16, No. 1 (Jul. 1990) pp. 145–154.

Pandian et al., "Intracardiac, Intravascular, Two–Dimensional, High–Frequency Ultrasound Imaging of Pulmonary Artery and Its Branches in Humans and Animals", *Circulation*, vol. 81, No. 6 (Jun. 1990) pp. 2007–2012.

Bom et al., "Early and Recent Intraluminal Ultrasound Devices", *International Journal of Cardiac Imaging*, vol. 4 (1989) pp. 79–88.

Schwartz et al., "Intracardiac Echocardiographic Guidance and Monitoring During Aortic and Mitral Balloon Valvuloplasty: In Vivo Experimental Studies", Abstract, *JACC*, vol. 15, No. 2, 104A (Feb. 1990).

Pandian et al., "Real–Time, Intracardiac, Two–Dimensional Echocardiography. Enhanced Depth of Field with a Low–Frequency (12.5 MHz) Ultrasound Catherter", *Echocardiography*, vol. 8, No. 4, (1991)pp. 407–422.

Hung et al., "Usefulness of Intracardiac Echocardiography in Transseptal Puncture During Percutaneous Transvenous Mitral Commissurotomy", Section of Cardiology, Chang Gung Med. Col. and Chang Gung Memorial Hospital, (May 10, 1993) p. 853.

Weintraub et al., "Intracardiac Two–dimensional Echocardiography in Patients with Pericardial Effusion and Cardiac Tamponade", *Journal Am Soc. of Echocardiography*, vol. 4, No. 6, (Nov.–Dec. 1991)pp. 571–576.

Schwartz et al., "Intracardiac Echocardiographic Imaging of Cardiac Abnormalities, Ischemic Myocardial Dysfunction, and Myocardial Perfusion: Studies With a 10 MHz Ultrasound Catheter", *Journal Am Soc. of Echocardiography*, vol. 6, No. 4, (Jul.–Aug. 1993)pp. 345–355.

Rothman et al., "Intraluminal Ultrasound Imaging Through a Balloon Dilation Catheter in an Animal Model of Coarctation of the Aorta", *Circulation*, vol. 85, No. 6 (Jun. 1992)pp. 2291–2295.

Tardif et al., "Intracardiac Echocardiography With a Steerable Low–Frequency Linear–Array Probe for Left–Sided Heart Imaging From the Right Side; Experimental Studies" *Journal Am. Soc. of Echocardiography*, vol. 8, No. 2 (Mar.–Apr. 1995)pp. 132–138.

Schwartz et al., "Intracardiac echocardiography without fluoroscopy: Potential of a balloon–tipped, flow–directed ultrasound catheter", *Am. Heart Journal*, vol. 129, No. 3 (Mar. 1995)pp. 598–603.

Kremkau, Frederick, "AAPM Tutorial. Multiple–Element Transducers", *RadioGraphics*, (Sep. 1993)pp. 1163–1176.

Belohlavek et al., "Three–and Four–Dimensional Cardiovascular Ultrasound Imaging: A New Era for Echocardiography", *Mayo Clin Proc.*, vol. 68 (Mar. 1993)pp. 221–240.

Seward et al., "Multiplane Transesophageal Echocardiography: Image Orientation, Examination Technique, Anatomic Correlations, and Clinical Applications", *Mayo Clin Proc.*, vol. 68 (Jun. 1993)pp. 523–551.

Bom et al., "Intravascular Ultrasound: Newest Branch of the Echo–Tree", *Cardiovascular Imaging*, vol. 4 (1992)pp. 55–59.

Schwartz et al., "Intracardiac echocardiography during simulated aortic and mitral balloon valvuloplasty: In vivo experimental studies", *Am. Heart Journal*, vol. 123, No. 3 (Mar. 1992)pp. 665–674.

Steward, et al., "Ultrasound Cardioscopy: Embarking on a New Journey", *Mayo Clin Proc.*, vol. 71, No. 7, (Jul. 1996), pp. 629–635.

Kossoff, et al., "Real–time quasi–three–dimensional viewing in sonography, with conventional, gray–scale volume imaging", *Ultrasound Obstet. Gynecol.*, vol. 4, (1994), pp. 211–216.

Entrekin, et al., "Real–time 3–D ultrasound imaging with a 1–D 'fan beam' transducer array", *SPIE*, vol. 1733 (1993), pp. 264–272.

Smith, et al., "High-Speed Ultrasound Volumetric Imaging System—Part I: Transducer Design and Beam Steering", *IEEE Transactions On Ultrasonics, Ferroelectrics, and Frequency Control*, vol. 38, No. 2 (Mar. 1991), pp. 100–108.

von Ramm, et al., "High-Speed Ultrasound Volumetric Imaging System—Part II: Parallel Processing and Image Display", *IEEE Transactions On Ultrasonics, Ferroelectrics, and Frequency Control*, vol. 38, No. 2 (Mar. 1991), pp. 109–115.

Devonald, et al., "Volume Imaging: Three-Dimensional Appreciation of the Fetal Head and Face", *J. Ultrasound Med.*, vol. 14 (1995), pp. 919–925.

Talbert, D.G., "An 'Add-On' Modification for Linear Array Real Time Ultrasound Scanners to Produce 3 Dimensional Displays", Conference: Ultrasonics International 1977, Brighton, England (28–30 Jun. 1977), copy 128/916, pp. 52–67.

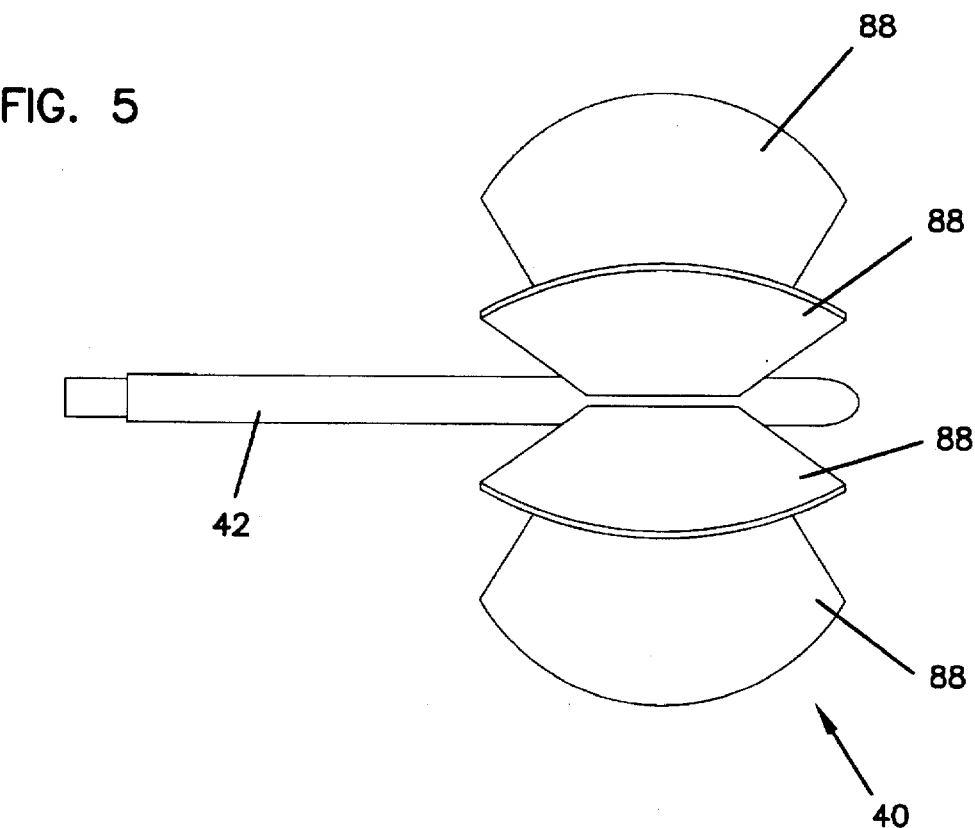
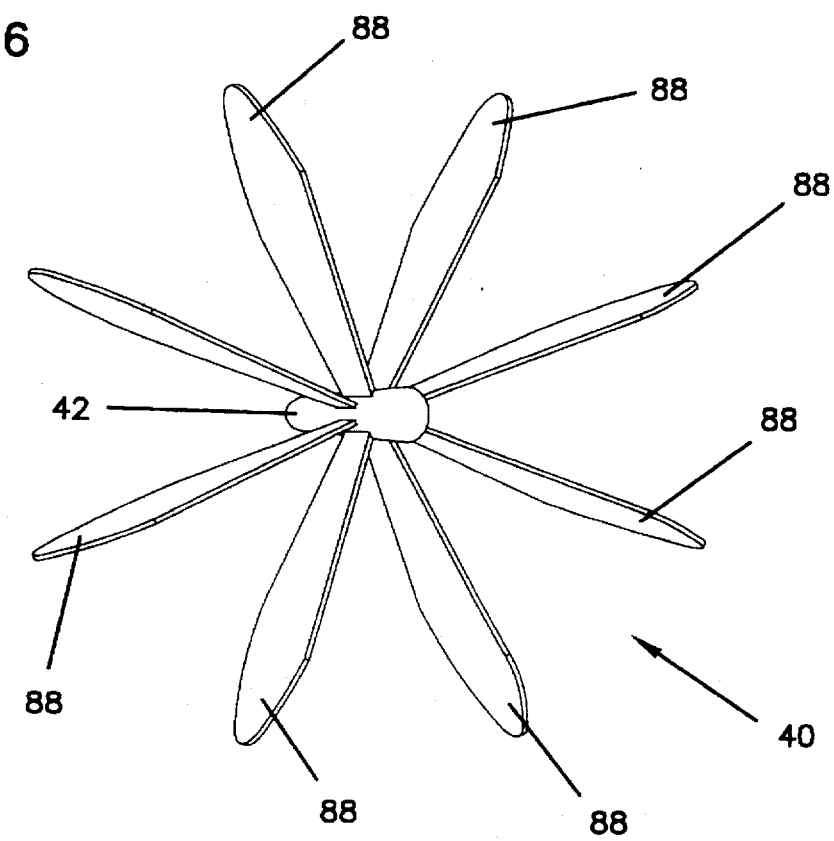

LONGITUDINAL MULTIPLANE ULTRASOUND TRANSDUCER UNDERFLUID CATHETER SYSTEM

FIELD OF THE INVENTION

The present invention relates generally to a volumetric, 3-dimensional imaging underfluid catheter system, particularly, to a catheter-based ultrasound imaging device having a longitudinally positioned, rotatable ultrasound transducer array.

BACKGROUND OF THE INVENTION

In the catheter-based imaging arena, increasing emphasis is being placed on intraluminal/intracavitary underfluid imaging for the purpose of directing precision therapy and diagnostics. Imaging systems generally operate by transmitting waves of ultrasonic energy into a body and receiving echoes returned from tissue interfaces upon which the waves impinge. The received echo information is typically translated/integrated into two-dimensional images that are representative of thin planar slices of the body structure being scanned.

While conventional two-dimensional imaging systems have proved to be very important diagnostic tools, it has been recognized that catheter based imaging systems capable of generating wider fields of view would greatly enhance a physicians ability to locate and diagnose anatomic features and contiguous structures within a body. Non-catheter systems typically depend upon the manipulation or rotation of an entire instrument, such as an entire endoscope shaft, to generate three-dimensional images. However, due to the tortuous and confined nature of a typical catheter pathway, catheter rotation is impractical and often impossible. Furthermore, catheter rotation, in most cases, would preclude three-dimensional image acquisition because of catheter translocation and loss of spacial relationship between individual planar slices of the body structure.

There is presently a need in the art for a catheter-based intraluminal/intracavital imaging device capable of generating wide fields of view while requiring no rotational manipulation of the catheter. There is also a need for a catheter based imaging device capable of providing multiple, spatially-related two-dimensional tomographic images of body structure that radially and longitudinally surrounds the catheter. There is further a need for a catheter based imaging device capable of generating a toroidal image of body structure that radially and longitudinally surrounds the catheter.

SUMMARY OF THE INVENTION

The present invention relates generally to a volumetric, 3-dimensional imaging underfluid catheter system.

The present invention also relates to a catheter-based ultrasound imaging device having an ultrasound transducer array positioned longitudinally along the catheter. The transducer array is constructed and arranged to generate a plurality of spatially-related two-dimensional tomographic images of body structure that longitudinally and radially surrounds the catheter. A significant feature of the device is that the spatially-related tomographic images can be generated without rotating the catheter. It will be appreciated that the images can be coalesced to generate a three-dimensional image, such as a toroid-shaped image, of the body structure that laterally surrounds the catheter.

In one particular embodiment, the invention relates to a catheter including an ultrasound transducer array mounted within the catheter and oriented along a longitudinal axis of the catheter. The ultrasound transducer array is connected to a drive shaft having an axis of rotation along the longitudinal axis of the catheter. By rotating the drive shaft, the transducer array is rotated relative to the catheter thereby enabling a sequence of spatially related tomographic image planes to be generated radially about the catheter. A sequential series of spatially related tomographic planes (i.e., a data set) can be used to produce a 3-dimensional volume image or field of view.

In another embodiment, the present invention is directed to a catheter including a plurality of ultrasound transducer arrays mounted on the catheter and extending longitudinally along a longitudinal axis of the catheter. The transducer arrays are spaced radially about the longitudinal axis of the catheter. The ultrasound arrays are connected to a drive shaft having an axis of rotation aligned along the longitudinal axis of the catheter. The drive shaft is used to rotate the ultrasound arrays relative to the catheter. By continuously or intermittently scanning while the ultrasound arrays are rotated relative to the catheter, a plurality of spatially related tomographic image planes are generated radially about the catheter. As with the aforementioned embodiment, sequential data sets from the series of spatially related tomographic planes can be used to generate a 3-dimensional volume image or field of view.

Catheters constructed in accordance with the present invention can include a window portion that covers the ultrasound transducer array and that is substantially transparent to ultrasound signals. The window portion can be disposed about the entire circumference of the catheter so as to allow transmission of ultrasound signals a full 360° about the catheter body.

Catheters constructed in accordance with the principles of the present invention can also include one or more longitudinal transporting ports for receiving and guiding medical instrumentation such as diagnostic or therapeutic devices. Exemplary medical instrumentation includes catheters, angiographic catheters, ablation catheters, cutting tools, blades and balloons. The longitudinal transporting ports can also be used to deliver medical drugs to localized regions of the body. It is preferred for the ports to have exit openings adjacent to the field of view of the transducer array so that the operation of the therapeutic or diagnostic device and the reaction therefrom can be observed in a real-time fashion.

It will be appreciated that catheters constructed in accordance with the principles of the present invention can include two-dimensional ultrasound transducer arrays for generating tomographic images and three-dimensional ultrasound transducer arrays for generating volumetric images. The transducer arrays can have a variety of conventionally known configurations. For example, the most common transducer array is configured to generate a fan shaped sector image. The array can also be a linear phased array having a rectangular shaped image, or other types of arrays, e.g. having a rhomboidal shaped images. Further, the ultrasound transducer array can be composed of one row or multi-rows of piezoelectric crystals. In another embodiment, the ultrasound transducer array can be composed of crystals having equal number of rows and columns. Tomographic (two-dimensional) and volumetric (three-dimensional) image arrays can obtain single or multiple planes depending upon the intended operation (i.e., no rotation or rotation).

These and various other advantages and features of novelty which characterize the invention are pointed out with particularity in the claims annexed hereto and forming a part hereof. However, for a better understanding of the invention, its advantages and objects obtained by its use, reference should be made to the drawings which form a further part hereof, and to the accompanying descriptive matter, in which there is illustrated and described a preferred embodiment of the invention.

BRIEF DESCRIPTION OF THE DRAWINGS

The accompanying drawings, which are incorporated in and constitute part of this specification, illustrate several embodiments of the present invention and together with the description, serve to explain the principles of the invention. A brief description of the drawings is as follows:

FIG. 5 is a schematic side view of a series of radially spaced spatially related tomographic image planes that are generated around a catheter system constructed in accordance with the principles of the present invention;

FIG. 6 is a perspective view of the catheter system and image planes of FIG. 5;

DETAILED DESCRIPTION OF THE PREFERRED EMBODIMENT

Figure 1:
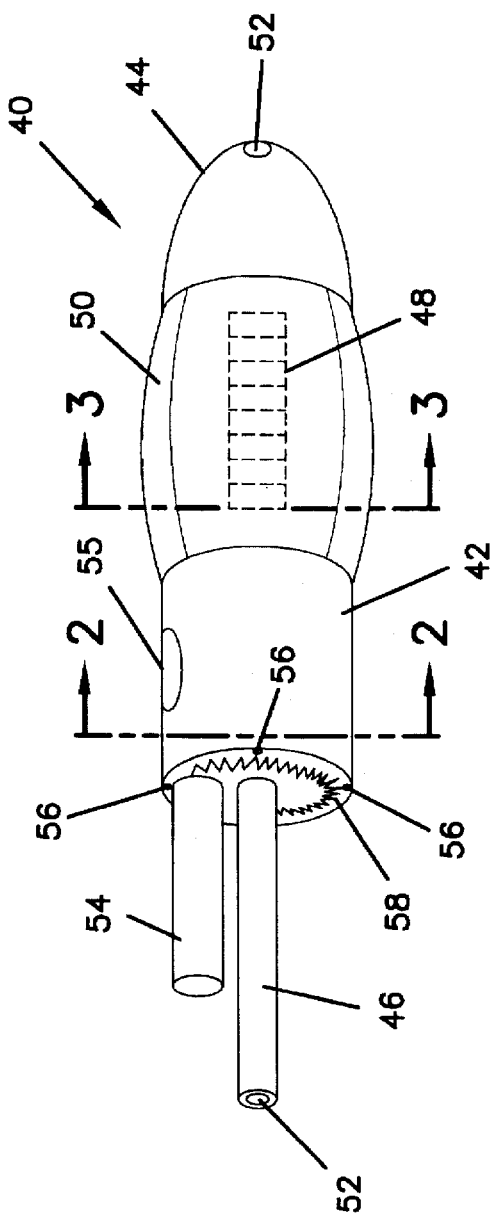
FIG. 1 is a partial schematic view of an embodiment of a catheter system in accordance with the principles of the present invention.

Referring to FIG. 1, a catheter system 40 (a partial view) is shown in accordance with the principles of the present invention. The catheter system 40 has a catheter body 42. The catheters generally disclosed in U.S. Pat. Nos. 5,325,860 and 5,345,940, issued to Seward, et al., are hereby incorporated by references for other parts of the catheter system 40 which are not shown in FIG. 1.

The catheter body 42 is an elongated flexible body which can be inserted into underfluid cavities of a body structure. The catheter body 42 has a distal end 44 and a proximal end (at the other side of the catheter body 42 which is not shown here). The catheter body 42 is substantially opaque to ultrasound.

In the embodiment shown in FIG. 1, a drive shaft 46 is generally disposed along a longitudinal axis of the catheter body 42 and is rotatable with respect to the catheter body 42 about the longitudinal axis. An ultrasound transducer array 48 is mounted adjacent to the distal end 44 of the catheter 42. The array 48 is mounted within the catheter body 42 and is rotatable about the longitudinal axis relative to the catheter body 42. A torque transmitting relationship exists between drive shaft 46 and the transducer array 48. For example, the drive shaft 46 could be fixedly connected to the array 48 by conventional bonding techniques. Alternatively, the drive shaft 46 could be interconnected with the array 48 via a gear mechanism or other assembly suitable for transmitting torque.

As described in the previous paragraph, a torque transmitting relationship exists between the drive shaft 46 and the transducer array 48. Consequently, the transducer array 48 is rotated relative to the catheter body 42 by rotating the drive shaft 46 about the longitudinal axis. In other words, the transducer array 48 is rotatable driven about the longitudinal axis of the catheter 42 by the drive shaft 46. It will be appreciated that a manual, mechanical or electrical linkage can be used to rotate the drive shaft 46. An exemplary a mechanical linkage includes a conventional micromotor that can be mounted either inside or outside the catheter body 42. By using electronic or mechanical mechanisms to rotate the transducer array 48 relative to the catheter 42, the transducer array 42 can be rotated in precisely controlled incremental advancements.

The catheter body 42 has an ultrasound window portion 50 proximate the distal end 44 of the catheter body 42. The window portion 50 faces laterally of the catheter body 42 and extends longitudinally along the catheter body 42. The ultrasound transducer array 48 is longitudinally positioned within the catheter body 42 proximate the window portion 50. The ultrasound window portion 50 is substantially transparent to the ultrasound signals transmitted from the array 48 and is echo lucent so as to allow the passage of ultrasound signals both in and out of the catheter body 42. The ultrasound window 50 allows signals from the ultrasound transducer array 48 to be projected radially outward from the side of the catheter body 42 such that a volumetric region is imaged radially about the catheter body 42. In this manner, rather than being forward looking, the array 48 provides a lateral or side field of view that radially surrounds the catheter 42.

It will be appreciated that the ultrasound window portion 50 can have varying sizes and configurations. In a preferred configuration, the window portion 50 is disposed radially about the entire circumference of the catheter body 42 so as to allow transmission of ultrasound signals a full 360° about the catheter body 42. Alternatively, the window portion 50 might extend about only a portion of the catheter body circumference to create a more limited circumferential field of view about the catheter body. For example, there might be a plurality of windows spaced apart and radially disposed about the circumference of the catheter body 42 so as to allow transmission of ultrasound signals from the transducer array 48 to the outside of the catheter body 42 at these spaced apart locations.

It will also be appreciated that the window 50 can be made of varying materials depending upon the desired function. Exemplary functions include transducer protection, focusing and defocusing. Exemplary materials include plastic or rubber.

The ultrasound transducer array 48 is preferably a linear phased array (also called a sector array) including aligned piezoelectric crystals that are electronically actuated in a particular sequence. The array 48 is preferably longitudinally disposed along the length of the catheter body 42. A single row of crystals can create image planes having variable shaped sectors. Exemplary sector shapes include pie/fan shaped, rectangular and rhomboidal. Transducers having multiple rows of crystals can be used to form either tomographic or volumetric images. The ultrasound frequencies employed by the transducer array 48 are variable. A preferred frequency range for intravascular scanning is 15 to 40 MHz. A preferred frequency range for intracavitary scanning 3.5 to 15 MHz.

As is further shown in FIG. 1, a guidewire port 52 is disposed in the drive shaft 46 along its longitudinal axis for delivering a guide wire to the front tip of the catheter body 42. The guidewire port 52 extends from the proximal end to the distal end 44 of the catheter body 42. Although the guide wire port 52 is shown extending through the drive shaft 46, it will be appreciated that guide wire ports can be longitudinally positioned within the catheter body 42 at any location that does not interfere with the rotation of the transducer array 48.

As is also shown in FIG. 1, a working port 54 is disposed in the catheter body 42 for delivery of medical instrumentation or drugs into the field of view formed by the array 48. The working port 54 extends from the proximal end to the distal end 44 of the catheter body 42 and has an exit end 55 adjacent to or within the field of view of the transducer array 48. Consequently, medical instrumentation that is passed through the working port 54 will project into the field of view of the array 48. Thus, the operation and manipulation of such medical instrumentation can be observed by a remote operator outside of a body structure via a plurality of real-time, 2-dimensional and 3-dimensional volumetric images around the catheter body 42.

Figure 2:
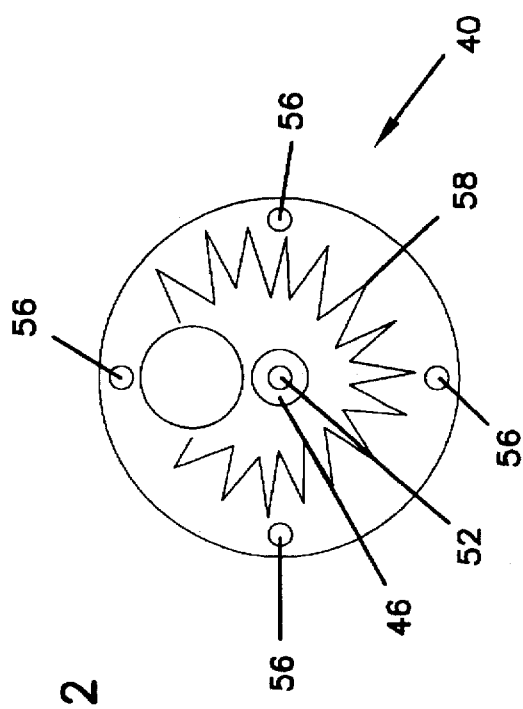
FIG. 2 is a cross-sectional view along line 2—2 of FIG. 1.

FIG. 2 shows a cross-sectional view along 2—2 of FIG. 1. A plurality of directional cables 56, e.g. 4-way flexion cables, are disposed in the catheter body 42. In addition, a plurality of flexwires 58 are disposed in the catheter body 42 for the electronic connection of the ultrasound transducer array 48 to a control circuit.

Figure 3:
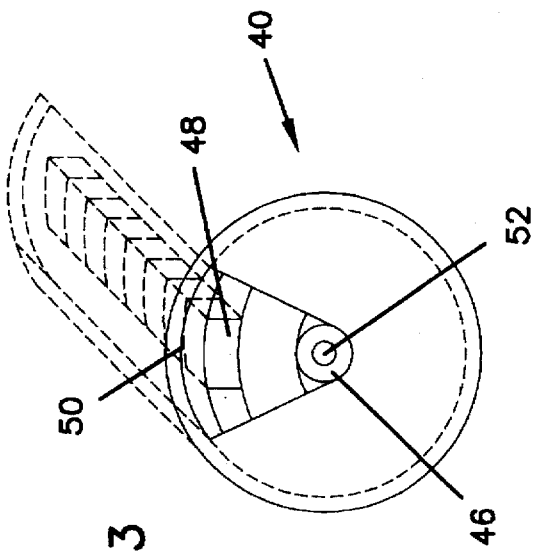
FIG. 3 is a cross-sectional view along line 3—3 of FIG. 1.

FIG. 3 is a cross-sectional view along 3—3 of FIG. 1, wherein the ultrasonic window portion 50 of the catheter body 42 fits around the array 48 like a sheath so as to allow rotation of the array 48 relative to the catheter body 42.

The catheter body 42 might have various diameters preferably varying from 4 to 15 French, and various lengths preferably varying from 40 to 130 centimeters. The guidewire port 52 preferably varies from 0.025 to 0,038 inches in diameter. It will be appreciated that other dimensions can be used within the principles of the present invention.

Figure 4:
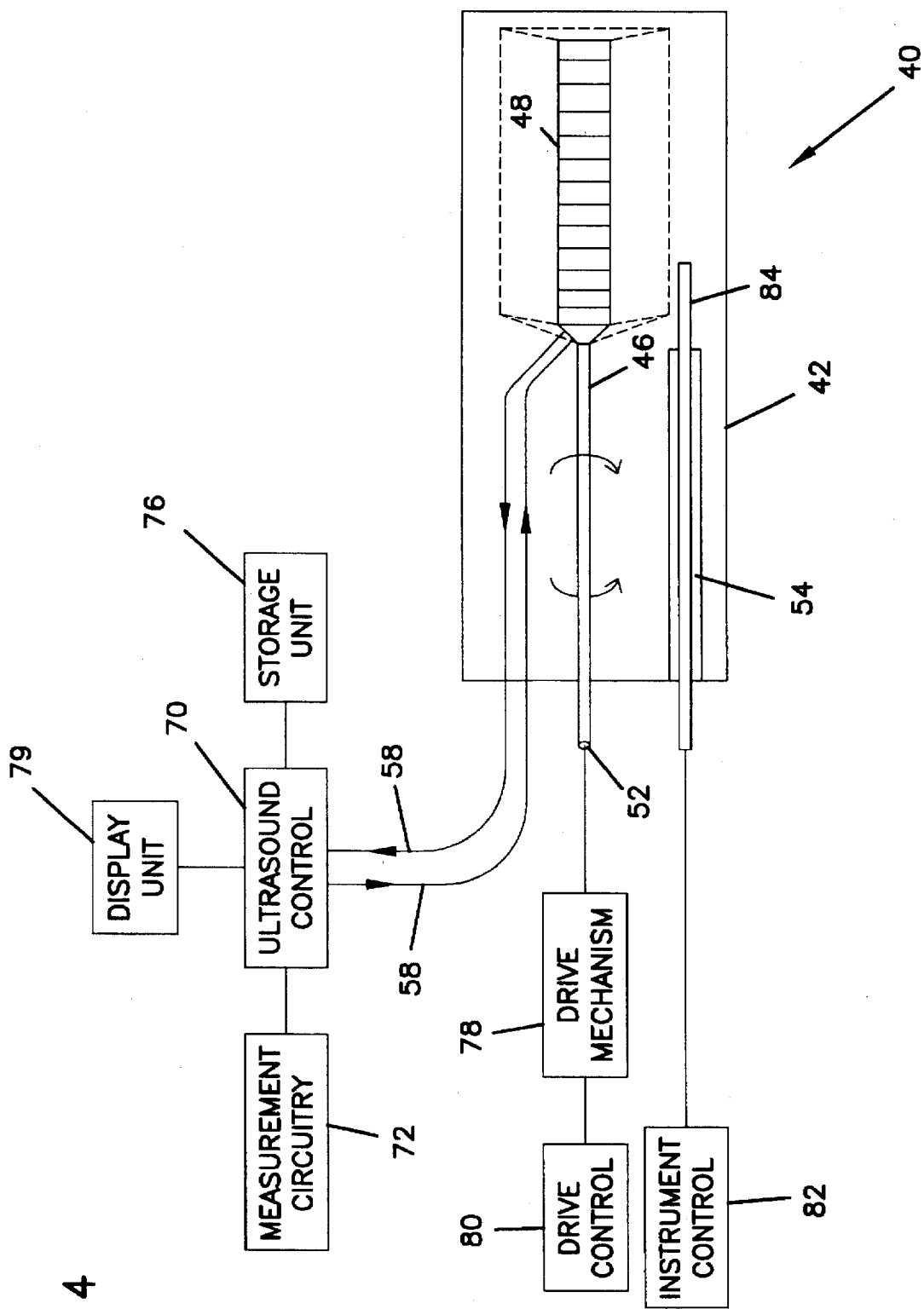
FIG. 4 is a block diagram illustrating the control system and component parts of the catheter system.

FIG. 4 shows a block diagram illustrating an exemplary control system for the catheter system 40. The control system includes a conventional ultrasound unit 70 capable of a variety of known functions. Exemplary functions include color flow Doppler, continuous and pulsed wave Doppler, tissue characterization, harmonic echocardiography and etc. The ultrasound control unit 70 is electronically coupled to the transducer array 48 via flexwires 58. The ultrasound control unit 70 is also coupled to conventional measurement circuitry 72 for measuring data generated by the ultrasound unit 70. Real-time images generated by the ultrasound unit 70 can be displayed on a conventional display unit 74 such as a video monitor. If desired, data generated by the ultrasound unit 70 can be stored for later analysis via a conventional data/image storage device 76.

The control system of FIG. 4 also includes a drive mechanism 78, such as a micromotor, that is mechanically coupled to the drive shaft 46. The drive mechanism 78 is constructed to rotate the drive shaft 46 about it's longitudinal axis in either a clockwise or counterclockwise direction. The mechanical nature of the drive mechanism 78 allows the drive shaft 46 to be rotated in precise incremental movements about it's longitudinal axis. It will be appreciated that the drive mechanism 78 can either be positioned within the catheter body 42 or can be remotely located from the catheter body 42.

The control system further includes a conventional drive control unit 80 that is electronically coupled to the drive mechanism 78. The drive control unit 80 is remotely located from the catheter body 42 and allows a physician to precisely control the drive mechanism 78 such that the transducer array 48 can be moved to a precise angular position relative to the catheter body 42. The control system also includes conventional instrument control 82 for allowing the physician to control medical instrumentation 84 that is inserted within the working port 54 of the catheter body 42. The instrument control 82 is remotely located from the catheter body 42.

Generally, the catheter system 40 is used for imaging within fluid-filled cavities such as blood vessels the heart, and the urinary bladder, and within confined spaces such as the esophagus, vagina and urethra. In use, the catheter body 42 is typically introduced into a cavity or vessel usually via a venous or arterial puncture. The imaging end of the catheter 42, which includes the transducer array 48, is then negotiated through the vessel or cavity. As the catheter 42 is moved though the vessel or cavity, the ultrasound controller 70 and the side-viewing longitudinal transducer array 48 cooperate to generate a real-time image of the body structure that is laterally adjacent to the transducer array 48.

When the imaging end of the catheter 42 is oriented a desired position, multiple longitudinal views can be obtained radially around the catheter 42 by rotating the transducer array 48 via the drive control 80, drive mechanism 78, and the rotatable drive shaft 46. The rotation of the transducer array 48 is accomplished without requiring rotation of the catheter body 42 and without the associated catheter translocation which results in loss of spatial relationships between consecutive radially spaced longitudinal views.

Figure 7:
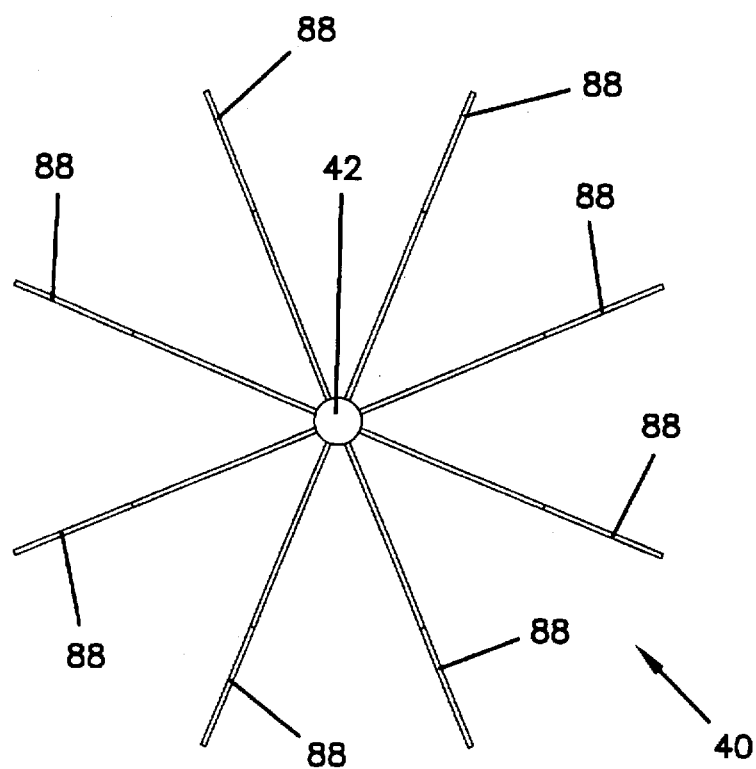
FIG. 7 is a front view of the catheter system and image planers of FIG. 5.

The drive control 80 allows the transducer array 48 to be incrementally and precisely rotated to specific angular positions relative to the catheter body 42. Because the transducer array 48 is precisely rotated without requiring rotation of the catheter, a precise spacial relationship is maintained between each of the angular positions. At each angular position, the ultrasound transducer array 48 projects an ultrasonic beam through the ultrasonic window 50 and laterally outward from the catheter to produce a longitudinal scanning sector extending radially outward from catheter 42. As shown in FIGS. 5–7, a plurality of fan-like scans are projected through the ultrasound window portion 50 of the catheter 42 to generate a plurality of spatially related longitudinal 2-dimensional tomographic image planes 88. The transducer array configuration can be varied to generate 2-dimensional scans of varying shapes and also to generate 3-dimensional scans. The width of the scanned image planes that pass through the window portion 50 depends on the width of the window 50, the degrees of rotation of the imaging array 48 and the array size. Each factor can be variably configured.

To obtain a 360° image radially around the catheter 42, the ultrasound transducer array 48 is incrementally rotated 360° by the drive shaft 46. At each radial increment, a new image is generated. FIGS. 5–7 show the resulting a sequence of longitudinal tomographic image planes 88. The image planes 88 are spatially related to each other and can be analyzed in the 2-dimensional configuration. Alternatively, the spatially related planes 88 can be electronically coalesced into a 3-dimensional volume images via conventional 3-dimensional reconstruction software that merge the spatially related planes.

Figure 8:
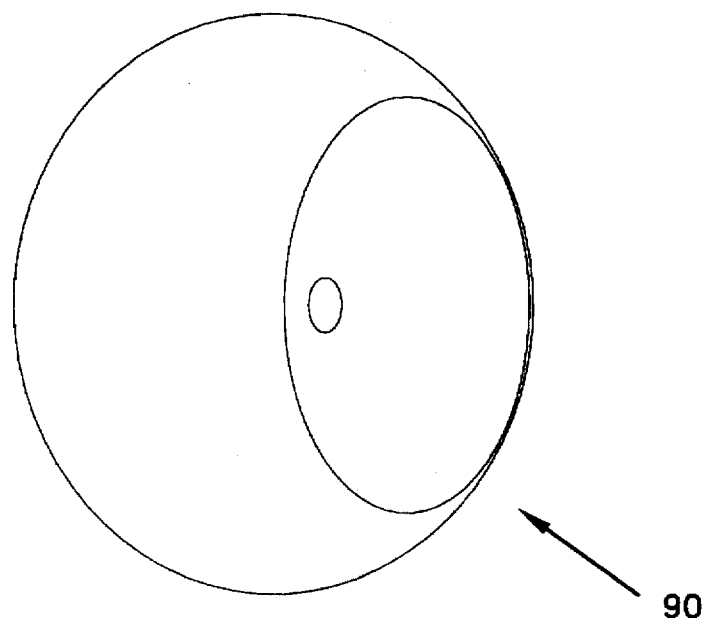
FIG. 8 is a perspective view of a toroid or doughnut-shaped field of view generated by coalescing a sequence of substantially overlapping longitudinal tomographic image planes.

In FIG. 8, there is shown a sequential set of tomographic image planes that have been merged to generate a volumetric representation of the scanned structure. As shown in FIG. 8, the volumetric image has a toroid 90 or doughnut shape. It will be appreciated that by vary the shape of the sequential scanning sectors, alternative volumetric shapes can be generated. It will also be appreciated that during the merging process, gaps between consecutive radially spaced tomographic planes are filled by interpolating statistically derived data between the consecutive tomographic planes. Consequently, the smaller the incremental angle between each consecutive tomographic plane, the greater the resolution of the subsequently generated 3-dimensional image. Additionally, it is not necessary for a full 360° field of view to be generated. If desired, images can be generated with respect to more limited regions surrounding the catheter 42. For example, the present invention can be used to generate 180° fields of view, 90° fields of view, or any other angular field of view.

It will be appreciated that catheter system 40 can be constructed and arranged such that the transducer array 48 includes a plurality of ultrasound transducer arrays mounted on the catheter 42 and extending longitudinally along a longitudinal axis of the catheter 42. The transducer arrays would preferably be spaced radially about the longitudinal axis of the catheter and connected to the rotatable drive shaft 46. The drive 46 provides a means for simultaneously rotating each of the arrays relative to the catheter 42. By continuously or intermittently scanning while the arrays are rotated relative to the catheter 42, a plurality of spatially related tomographic image planes can be generated radially about the catheter 42. As previously described, sequential data sets from the series of spatially related tomographic planes can be used to produce a 3-dimensional volume image or field of view.

It will be appreciated that the transducer arrays can be sequentially actuated via any number of conventionally known electronic control units or control circuits. Such sequential activation of the radial spaced arrays would typically be used to form volumetric images having angular fields of view less than 360°.

Specific examples of clinical applications of the present invention are:

1) Intracardiac: Conventionally, ultrasound transducer tipped catheters that are placed within a heart chamber must be manipulated by repositioning the catheter tip. This can be logistically difficult and cumbersome because of the confined space, impingement of cardiac walls, potential induction of rhythm disturbances, etc.

For a variety of reasons, catheters constructed in accordance with the present invention are ideally suited for imaging tubular structures such as the heart, blood vessel, or other lumen (such as the esophagus, urethra, ureter, vagina, etc.). For example, a phased sector array employed by the present invention has a larger field of view with a relatively smaller transducer size. Also, The ability to manipulate a transducer through multiple projections without catheter rotation or manipulation is particularly advantageous. Furthermore, because the transducer array can be rotated 360°, information (including anatomy and function) can be obtained from all directions. Thus, a 360° rotatable longitudinal multiplane transducer array is very desirable in the medical and the other related applications. Additionally, the toroidal volumes generated by the present invention are better suited for visualizing contiguous structures and physical events such as blood flow or muscle contraction than are the conical and pyramidal volume images employed by prior art systems.

2) Intravascular: The present invention generates multiple, radially spaced longitudinal image (i.e. linear phased array) around a catheter without requiring rotation of the delivery catheter. Because the image is obtained from within small fluid-filled structures, the ability to generate a 360° field of view around the catheter without rotating the catheter is important.

3) Fluid-filled cavities: Other body cavities such as the urinary bladder, gallbladder, bile ducts, pleural space, peritoneal cavity, etc., are suited for this form of multiplane transducer. With the transducer inside the cavity there is potential information in all directions.

4) Luminal imaging: The esophagus, urethra, vaginal vault, ureter, etc., are also suited to 360° image acquisition. The present invention uses rotation to provide a plurality of radially spaced tomographic planes that extend longitudinally along the length of the catheter. Consequently, when the images are merged, an image volume is generated.

5) 3-dimensional imaging: The present invention is unique because it proposes an automated longitudinal multiplane acquisition. Image volumes (e.g. pyramidal) have previously been acquired by rotation of an entire transesophageal scope shaft. The present invention poses the possibility of obtaining very large volumes such as the toroidal image (i.e., a 360° acquisition) without requiring rotation of a catheter or scope. In addition, 3-dimensional volumetric images can be provided in real-time. Other iterations include the use of multiple longitudinal image array or a 2-dimensional volumetric array which is stimulated or rotated in a manner to obtain a partial or complete toroidal volumetric image.

6) Transcavity imaging: The concept of imaging surrounding tissues outside the cavity or vessel from within a fluid-filled space is also possible with the present invention. Ultrasound will penetrate the fluid-filled cavity and its walls and image the extracavitary anatomy and physiology.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

What is claimed is:

1. A catheter apparatus, comprising:
   a catheter including an outer body and a drive shaft receivable in the outer body and rotatable with respect to the outer body;
   a transducer phased array mounted on the drive shaft, the transducer phased array being rotatable with the drive shaft, the transducer phased array transmitting signals toward outside of the catheter; and
   the outer body having an ultrasound window portion at least partially transparent to the signals, the transducer phased array being longitudinally positionable within the outer body proximate the window portion.

2. A catheter apparatus according to claim 1, wherein when the transducer phased array transmits ultrasound signals, a sequential set of spatially related tomographic image planes are formed which define a volumetric field of view around the catheter.

3. A catheter apparatus according to claim 2, further comprising a port disposed in the catheter and extending from proximate a proximal end to proximate a distal end of the catheter for receiving medical instrumentation, the medical instrumentation being extended out of the port and operable within the volumetric field of view.

4. A catheter apparatus according to claim 3, wherein the sequential set of spatially related tomographic image planes substantially overlap with each other to provide an image area having a toroid shape.

5. A catheter apparatus according to claim 1, wherein the ultrasound window portion is disposed about an entire circumference of the catheter.

6. A catheter apparatus in accordance with claim 1, further comprising a guidewire port which is disposed in the drive shaft extending from proximate a proximal end to proximate a distal end of the catheter for receiving a guide wire.

7. A catheter apparatus in accordance with claim 1, wherein the transducer phased array is an ultrasound transducer array, the ultrasound transducer array being aligned generally along a longitudinal axis of the catheter.

8. A catheter apparatus in accordance with claim 1, wherein the transducer phased array is rotatable over 360° so as to provide a 360° image radially around the catheter.

9. A catheter apparatus, comprising:

a catheter including a catheter body having a longitudinal axis;

an ultrasonic transducer phased array mounted on the catheter body and oriented so as to extend longitudinally along the catheter, the transducer phased array being constructed and arranged for transmitting an ultrasonic signal radially outward from the catheter body; and image rotating structure for controlling a radial direction in which the ultrasound signal is transmitted from the ultrasonic transducer phased array, wherein the image rotating structure is constructed and arranged to rotate the radial direction in which the ultrasound signal is transmitted about the longitudinal axis of the catheter body without rotating the catheter body.

10. The catheter apparatus of claim 9, wherein the image rotating structure comprises a drive shaft rotatably mounted within the catheter body, the drive shaft being constructed and arranged for rotating the transducer phased array with respect to the catheter body about the longitudinal axis of the catheter body.

11. The catheter apparatus of claim 10, further comprising means for precisely controlling the rotation of the drive shaft.

12. The catheter apparatus of claim 10, wherein the image rotating structure comprises a control circuit.

13. The catheter apparatus of claim 9, wherein the catheter body includes an ultrasound window that covers the transducer phased array.

14. The catheter apparatus of claim 9, wherein the transducer phased array is rotatable over 360° so as to provide a 360° image radially around the catheter.

15. A method of imaging a cavity, comprising the steps of:

providing a catheter having a longitudinal axis and a transducer phased array mounted on the catheter and extending along the longitudinal axis;

positioning the catheter in the cavity;

generating a plurality of spatially related and radially spaced ultrasonic images around at least a portion of a circumference of the catheter without physically rotating the catheter.

16. The method of claim 15, further comprising the step of merging the ultrasonic images to form a volumetric image.

17. The method of claim 15, wherein the ultrasonic images are positioned around the entire circumference of the catheter.

18. The method of claim 17, further comprising the step of merging the ultrasonic images to form a toroidal image.

19. The method of claim 15, wherein the transducer phased array is rotatable over 360° so as to provide a 360° image radially around the catheter.

* * * * *